US005679658A

United States Patent [19]

Elson

[11] Patent Number: 5,679,658
[45] Date of Patent: Oct. 21, 1997

[54] N,O-CARBONXYMETHYLCHITOSAN FOR PREVENTION OF SURGICAL ADHESIONS

[75] Inventor: Clive M. Elson, Halifax, Canada

[73] Assignee: Chitogenics, Inc., Cedar Knolls, N.J.

[21] Appl. No.: 436,770

[22] Filed: May 8, 1995

[51] Int. Cl.$^6$ .......................... A61K 31/73; C08B 37/08; A61F 2/00

[52] U.S. Cl. .................... 514/55; 514/2; 514/8; 514/54; 536/20; 604/57; 424/422; 424/423; 424/424; 424/426; 424/488

[58] Field of Search .......................... 514/2, 8, 54, 55; 536/20; 604/57; 424/422, 423, 424, 426, 488

[56] References Cited

U.S. PATENT DOCUMENTS

| | | | |
|---|---|---|---|
| 4,141,973 | 2/1979 | Balazs | 424/180 |
| 4,619,995 | 10/1986 | Hayas | 536/20 |
| 4,819,617 | 4/1989 | Goldverg et al. | 128/897 |
| 4,886,787 | 12/1989 | De Belder et al. | 514/57 |
| 5,023,090 | 6/1991 | Levin | 424/520 |
| 5,080,893 | 1/1992 | Goldberg et al. | 514/57 |
| 5,093,319 | 3/1992 | Higham et al. | 514/55 |
| 5,140,016 | 8/1992 | Goldberg et al. | 514/57 |
| 5,411,988 | 5/1995 | Bockow et al. | 514/560 |
| 5,462,990 | 10/1995 | Hubbell et al. | 525/54 |

FOREIGN PATENT DOCUMENTS

93/13137   7/1993   WIPO .

OTHER PUBLICATIONS

Buckman, R.F., et al. (1976) "A physiologic basis for the adhesion-free healing of deperitonealizing surfaces" *J. Surg. Res.* 21:67–76, months not available.

Elkins, T.E. et al. (1984) "Adhesion prevention by solutions of sodium carboxymethylcellulose in the rat. I." *Fert. Ster.* 41:926–928; months not available.

Elkins, T.E. et al. (1984) "Adhesion prevention by solutions of sodium carboxymethylcellulose in the rat. II." *Fert. Ster.* 41:929–932; months not available.

Fukasawa, M., et al. (1991) "Inhibition of postsurgical adhesions in a standarized rabbit model: II. Intraperitoneal treatment with heparin" *Int. J. Fertil.* 36:296–301; months not available.

Gervin, A.S. et al. (1973) "Serosal Hypofibrinolysis. A cause of postoperative adhesions" *Am. J. Surg.* 125:80–87; months not available.

Hemaheh, O. et al. (1993) "Prevention of peritoneal adhesion by administration of sodium carboxymethylcellulose and oral vitamin E." *Surgery* 114:907–910; months not available.

Holtz, G. (1980) "Prevention of posoperative adhesions" *J. Rep. Med.* 24:141–146; months not available.

Langford, M.P. (1995) "Effects on Healon, N,O Carboxymethyl Chitosan and Vitreon on Conjunctival Cells and Human Peripheral Blood Lymphocytes" Southern Biomedical Engineering Conference –Proceedings 1995 IEEE, Piscataway, NJ, USA (pp. 286–288), months not available.

Levinson, C.J. and Swolin, K. (1980) "Postoperative adhesions: Etiology, prevention and therapy" *Clin. Obstet. Gynec.* 23:1213–1220; months not available.

Nair, S.K. et al. (1974) "Role of proteolytic enzymes in the prevention of post–operative intraperitoneal adhesions." *Arch. Surg.* 108: 849–853; months not available.

Sahin Y. and Saglam A. (1994) "Synergistic effects of carboxymethylcellulose and low molecular weight heparin in reducing adhesion formation in the rat uterine horn model" *Acta. Obstet. Gynecol. Scand.* 73: 70–73; months not available.

Sawhaney et al. (1994) "Optimization of photopolymerized bioerodible hydrogel properties for adhesion prevention" *J. Bio. Mat. Res.* 28:831–838; months not available.

Thompson, J.N. et al. (1989) "Reduced human peritoneal plasminogen activating activity: Possible mechanism of adhesion formation" *Br. J. Surg.* 76:382–384; months not available.

Hirano et al. "Proc. Symp. Adv. Biomed. Polym." 1987, 285–297, months not available.

Muzzarelli *Carbohydrate Polymers* 1988(8), 1–21, months not available.

*Primary Examiner*—Kathleen K. Fonda
*Attorney, Agent, or Firm*—Lahive & Cockfield, LLP

[57] ABSTRACT

The invention relates to a method of treating patients to minimize post-surgical adhesions and a kit useful in the method of the invention. The method is based on the timing that N,O-carboxymethylchitosan (NOCC) has advantageous properties as a wound healing lavage and coating. A NOCC solution is particularly effective as a post-surgical lavage and when used in conjunction with a NOCC gel coating, wound healing rate is unchanged while the number and severity of adhesions in greatly reduced.

15 Claims, 3 Drawing Sheets

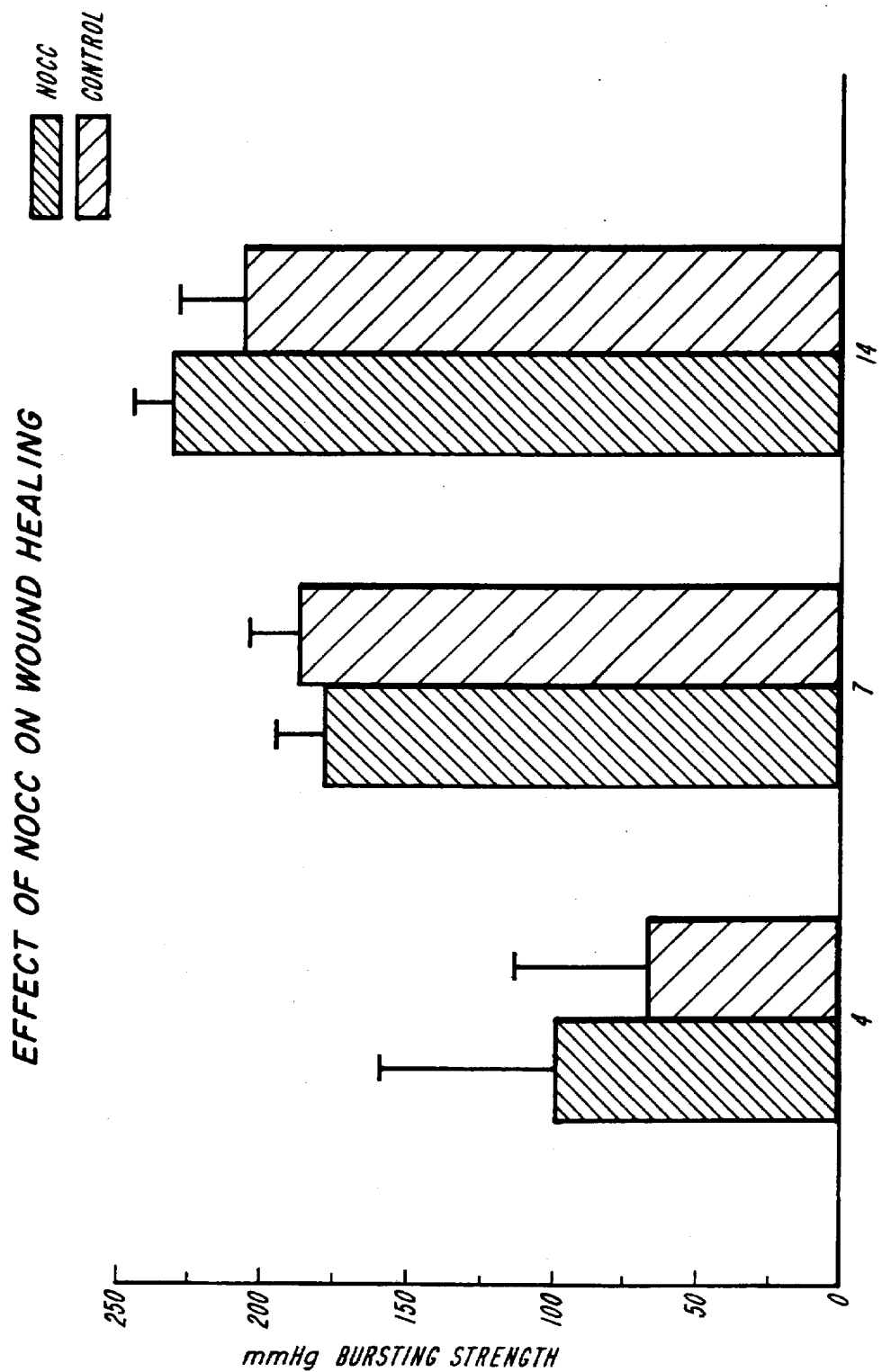

N,O-CARBONXYMETHYLCHITOSAN FOR PREVENTION OF SURGICAL ADHESIONS

BACKGROUND OF THE INVENTION

The present invention relates to the prevention and/or minimization of adhesions following surgery. The method of the invention uses a post-surgical lavage or wash of N,O-carboxymethylchitosan ("NOCC") which provides unexpected benefits in minimizing adhesion formation.

The problems associated with adhesions of tissues following surgery have been known for many years. These adhesions are caused by a combination of factors including manipulative trauma and drying of the tissues during the surgery itself. A number of techniques attempting to ameliorate these problems have been described. Highly concentrated solutions of a number of polymers have been used to coat the surgical area before, and during, surgery so as to minimize the drying and act as "cushion" to prevent some of the manipulative trauma. Examples of the techniques are described in U.S. Pat. No. 4,819,617, to Goldberg et al. and U.S. Pat. No. 4,886,787 to De Belder et al. Among the materials used included polyvinylpyrrolidone, dextrans, carboxymethylcelluloses, and a number of other polymers such as protein or polypeptide solutions. One promising polymer which has been used is hyaluronic acid ("HA"). A series of patents by Goldberg et al., particularly U.S. Pat. No. 5,080,893 and U.S. Pat. No. 5,140,016, show the use of pretreatment of surgical sites with hyaluronic acid solutions as a means of preventing surgical adhesions.

Hyaluronic acid has several problems associated with its use. One problem with using hyaluronic acid is its cost. Further, hyaluronic acid is obtained from rooster combs or human umbilical cords, and requires substantial purification to make pure enough to use in surgical techniques. See e.g., U.S. Pat. No. 4,141,973, to Balazs, which describes methods of purifying hyaluronic acid. Even if the high cost and difficulties in purification can be justified, hyaluronic acid often has proteins associated with it which may cause tainting of the open surgical wound.

For certain non-surgical uses, some chitin or chitosan-based solutions have been tried in place of hyaluronic acid. This is because the polysaccharide structure of chitin is similar to the structure of hyaluronic acid. However, while hyaluronic acid is difficult to find and purify, chitin occurs in greater quantities than almost any other material in nature. Chitin is the primary building block of the shells of crustaceans and many insects. Because of its prevalence, chitin can be relatively cheaply obtained, primarily from waste products which otherwise would have to be disposed. U.S. Pat. No. 4,619,995, issued on an application by Hayes, describes a novel derivative of chitin, NOCC. NOCC has carboxymethyl substitutes on some of both the amino and primary hydroxyl site of the glucosamine units of the chitosan structure and can be used in an uncrossed linked form as a solution; it can be cross-linked or complexed into a stable gel. Because of its advantageous physical properties, and its relative low cost compared with materials like hyaluronic acid, NOCC presents advantageous properties for use in surgical techniques.

Accordingly, an object of the present invention is to use NOCC to minimize or ameliorate problems with surgical adhesions.

Another object to the invention is to use a NOCC solution in a post-surgical lavage as a means of preventing or ameliorating surgical adhesions.

Another object of the invention is to provide a combination treatment consisting of at least post-suturing treatment and post-surgical lavage in order to prevent or ameliorate surgical adhesions.

A still further object of the invention is providing a kit which may be used to assist surgeons in treatment of surgical adhesions.

These and other objects and features of the invention will be apparent from the following description and the drawing.

SUMMARY OF THE INVENTION

The present invention features a method of minimizing post-surgical adhesions and a kit which can be used to practice the methods of the invention. The invention is based, in part, on the discovery that a post-surgical lavage with a solution containing an effective amount of NOCC in a pharmaceutically acceptable carrier has advantageous properties in minimizing surgical adhesions. Further, it has been discovered that a combination therapy of applying a post-suturing, but pre-lavage, covalently cross-linked NOCC gel or a non-covalently complexed NOCC gel, followed by the post-surgical lavage with a NOCC solution, has even more advantageous properties.

The basic method of the invention comprises the step of post-surgical lavage of the surgery area with a solution containing NOCC in a pharmaceutically acceptable carrier. The term "post-surgical lavage", as used herein, means and implies a wash or flushing of the surgical site after suturing of the surgical incision but prior to closing of the skin at the surgical site. The amount of NOCC contained in the solution should be effective to reduce or minimize the number of surgical adhesions, preferably in the form of a 0.5–4% by weight solution, most preferably a 1–3% solution. The total amount of the NOCC used in the lavage should be approximately 100–300 mg/kg of body weight. Preferred pharmaceutically acceptable carriers include water, saline, phosphate buffered saline and mixtures thereof, but any other pharmaceutically acceptable carrier may be used.

The method or treatment of the invention can be enhanced by coating the surgical site with an effective amount of a covalently cross-linked NOCC gel or a non-covalently complexed NOCC gel post-suturing and prior to the lavage. The cross-linked NOCC gel is normally 0.1–3% by weight NOCC, most preferably 0.5–1.5% by weight. The NOCC gel can be formed as shown in U.S. Pat. No. 4,619,995 (the disclosure which is incorporated herein by reference). The gel can be cross-linked or complexed with multivalent ions, glyoxal and other dialdehydes, diketones, and other polyvalent organic and inorganic molecules. Covalent cross-linking, e.g., using glyoxal, is preferred. In some circumstances, the covalently cross-linked NOCC gel can be replaced with a 0.1–10% non-covalently complexed (or electrostatic cross-linked) NOCC gel, preferably a 2–6% by weight non-covalently complexed NOCC gel. This non-covalently complexed NOCC gel is made by complexing or cross-linking a NOCC solution with molecules having multiple positively charged centers, preferably polymers such as proteins, polylysine or chitosan. The non-covalently complexed gel is used in the same manner as the covalently cross-linked gel.

In some circumstances, adding a pre-surgical lavage to the post-surgical lavage and, possibly, the gel coating, is advantageous. A pre-surgical lavage is carried out after opening but prior to manipulation. The pre-surgical lavage should be similar in type to that used for the post-surgical lavage, preferably a NOCC solution in a pharmaceutically acceptable carrier. Again, a 0.5–4% by weight, most preferably 1–3% by weight, NOCC solution is preferred.

The invention further features a kit for treatment of surgical patients which can be used to minimize adhesions. The kit contains a solution of NOCC in a pharmaceutically acceptable carrier, preferably a 1–3% by weight solution. Preferably, a cross-linked NOCC gel, most preferably a 0.1–3% covalently cross-linked NOCC gel, is also included in the kit.

Further aspects of the invention will be apparent from the following detailed description of the invention and the drawing.

BRIEF DESCRIPTION OF THE DRAWING

FIG. 3 shows the effects of NOCC on wound healing in a bursting strength intestinal anastomosis model.

DETAILED DESCRIPTION OF THE INVENTION

Figure 1:
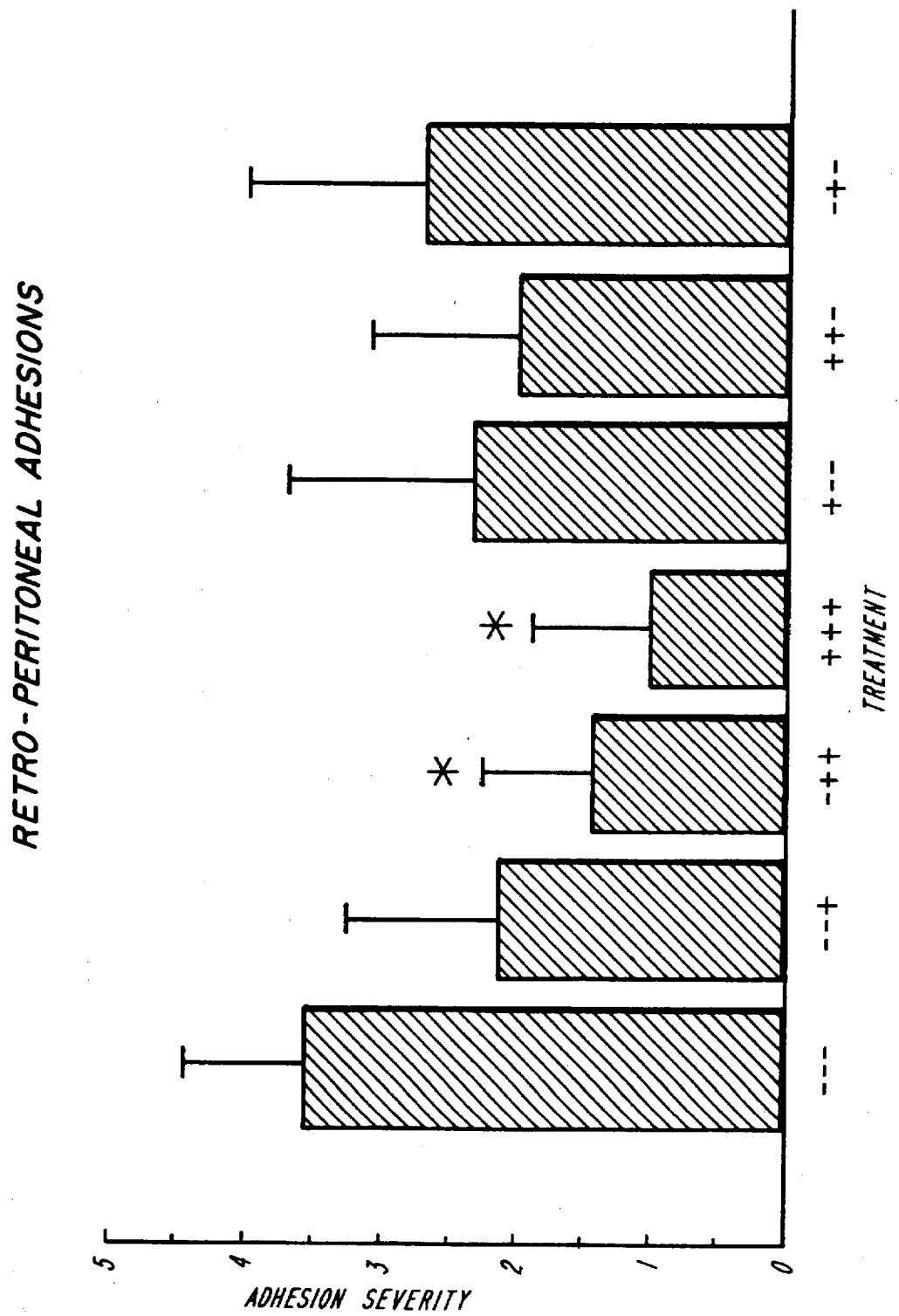
FIG. 1 is a bar graph showing a comparison of controls, pre-surgical application of a NOCC solution, pre-closure application of a NOCC gel, and post-surgical application of a NOCC solution, and all combinations thereof, on retroperitoneal adhesions from aortic surgery.

The present invention provides a method of minimizing post-surgical adhesions through the use of a NOCC solutions as a post-surgical lavage. Preferably, a pre-surgical lavage and a covalently cross-linked NOCC gel or a non-covalently complexed NOCC gel coating are also used to provide an even better anti-adhesion treatment. These methods are believed to reduce the adhesions by providing a reduction in wound site drying and manipulative trauma, factors which may lead to formation of adhesions. The use of the NOCC solution (and the NOCC gel) does not impede wound healing while reducing the adhesions. Further, despite its much lower cost, the use of NOCC compares favorably with hyaluronic acid treatment in minimizing adhesions.

In its broadest aspect, the invention merely employs a NOCC solution as post-surgical lavage of an anti-adhesion treatment. In preferred embodiments, a NOCC gel, preferably a covalently cross-linked NOCC gel, is used as a coating after surgical suturing but before the post-surgical lavage and wound closing as a protective coating in addition to the post-surgical lavage. In other aspects, a pre-surgical lavage may be used in addition to the post-surgical lavage.

The following, non-limiting examples will further elucidate the invention.

EXAMPLE 1

In this example, a standard abdominal adhesion model, the cecal abrasion model, was used to compare NOCC with hyaluronic acid in effectiveness of treatment. Twenty Sprague-Dawley rats, about 250–300 g each, were anesthetized with 20 mg/ml intraperitoneal pentobarbital. The abdomen was shaved and cleaned with a betadine solution and a lower midline abdominal incision was made. The cecum was identified and abraded with a dry 4×4 gauge needle until a punctate hemorrhage was noted. The wounds were closed with 4-0 silk sutures and covered with a topical placement of Bacitracin ointment. This model is further described in Sawhaney et al., J. Bio. Mat. Res. 28, 831–838 (1994).

The twenty rats treated as described above were divided into five groups of four animals each. Group 1 was designated a control and received no additional treatment. Group 2 received topical placement of a 1% NOCC solution, Group 3 received topical placement of a 2% NOCC solution, Group 4 received topical placement of a 1% NOCC gel covalently cross-linked with glyoxal, and Group 5 received a 0.4% hyaluronic acid placement. The test solutions were all placed on the hemorrhage site and the surrounding tissue. The animals were sacrificed after 7 days and the extent of abrasion was tested using a 0–3 scale with the following test criteria:

0-Normal Animal;
1-mild, transparent adhesions, normal pink serosa of the cecum;
2-adhesion on more than one surface of the cecum; and
3-severe, thick matted adhesion with the serosol surface scared with fibrous debris.

The results were analyzed by one-way analysis of variation and Duncan's Multiple Range test. Group 1, the control group, had a score of 3.0; Group 2, the 1% NOCC solution group, had a score of 0.61+ or −0.48; Group 3, the 2% NOCC group, had a score of 0.87+ or −0.85; Group 4, the 1% NOCC gel group, had a score of 0.12 + or −0.25; and Group 5, the hyaluronic acid group, had a score of 0.50+ or −0.4. Compared to the control animals, all the treated groups demonstrated significantly less adhesions ($p>0.05$). The difference among the groups, except for the control group, is not statistically significant. Accordingly, NOCC appears to be at least as good as the hyaluronic acid in this adhesion model.

EXAMPLE 2

In this example, an aortic anastomosis model was used to test the ability of NOCC to prevent abdominal adhesion formation. Tests were conducted using 3 ml of a 2% NOCC solution as a pre-surgical lavage, 1 ml of a 1% NOCC covalently cross-linked gel coating, 3 ml of a 2% NOCC solution as a post-surgical lavage, and all relevant combinations of the foregoing. In addition, a control without the NOCC was also used. Table 1 shows the treatment for each of the seven groups of eight rats each.

TABLE I

| | |
|---|---|
| 1. — — = | no NOCC treatment |
| 2. — + = | NOCC solution only after surgery |
| 3. — ++ = | NOCC gel as coating and NOCC solution after surgery |
| 4. +++ = | NOCC solution before surgery, NOCC gel as a coating and NOCC solution after surgery |
| 5. + — = | NOCC solution before surgery |
| 6. ++ — = | NOCC solution before surgery and NOCC gel as a coating |
| 7. — + — = | NOCC gel as a coating |

The experimental procedure for this aortic and anastomosis model is as follows:

Male Sprague-Dawley rats, weighing about 250–300 g each, were anesthetized with 30 mg/ml sodium pentobarbital using an intraperitoneal injection. A midline incision was made in the abdominal cavity and the abdomen exposed with stainless steel retraction. The animal was eviscerated to the left and the abdominal contents covered with saline-soaked gauze for the duration of the surgery. The aorta and vena cava were exposed just proximal to lumbar outflow and the vessels were carefully teased apart. The aorta was clamped proximal and distal to the suture site with microvascular clamps. The aorta was then sectioned with microsurgical scissors and the free ends immediately flushed with heparinized saline. The free ends were brought together with stay sutures at 9 o'clock and 3 o'clock and the aortic repair was accomplished with running sutures first on the back wall and then on the front wall. 10.0 sutures were used throughout. After the aorta was sutured, the clamps were removed and light pressure maintained on the resulting anastomosis for 1 minute after which bleeding subsided. When the animal was stabilized, the retractor was removed and the abdomen was closed with a running 4.0 suture. The skin was then closed with a running 3.0 suture.

For the pre-surgical lavage, 3 ml of a 2% NOCC solution was applied immediately after the abdomen was exposed by retraction. When the NOCC gel was used, 1 ml of a 1% NOCC gel was applied after successful anastomosis, while the post-surgical lavage of 3 ml of 2% NOCC solution was added immediately prior to the removal of the retractors and before closure. In all cases, the NOCC solution was applied evenly over the viscera, not just at the suture site.

The results were graded using a 0–5 standardized grading system for severity of adhesions. Table 2 shows the grating system used.

TABLE 2

| | |
|---|---|
| 0 = | absence of any visible adhesions |
| 1 = | thin filmy adhesion |
| 2 = | more than one thin adhesion |
| 3 = | thick adhesion attaching at a focal surface |
| 4 = | thick adhesions attaching at a planar rather than focal surface |
| 5 = | very thick vascularized adhesions or adhesions involving more than on planar |

Figure 2:
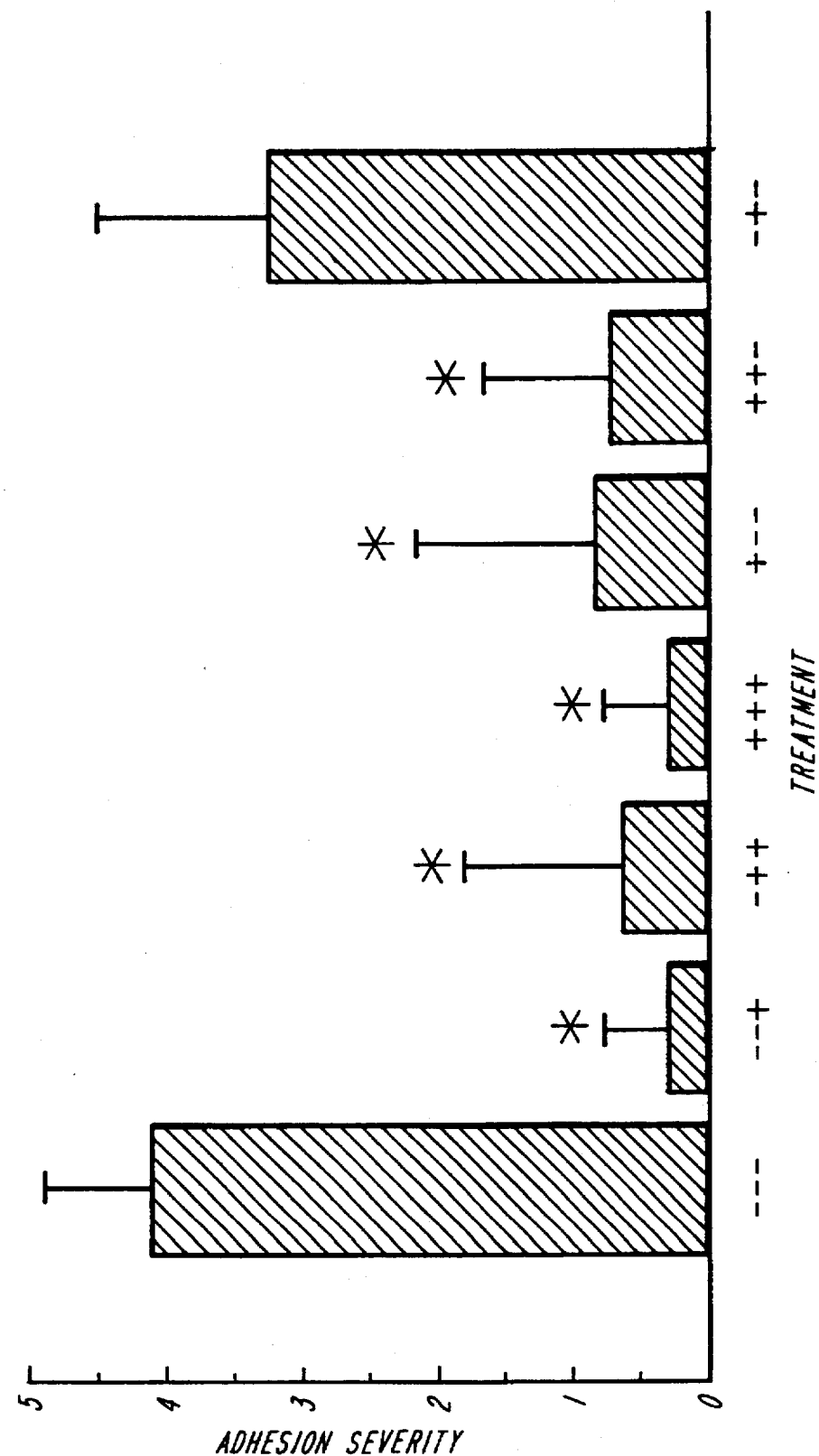
FIG. 2 is another bar graph which shows the same samples and their effects on liver adhesions.

A number of different sites were examined for adhesions. These include the retroperitoneal including the descending colon, the liver, the testicular fat pads, the omentum, and the small bowel. The results on the testicular fat pads, omentum and small bowel were not statistically significant. The significant results of the testing are shown in the Figures. FIG. 1 shows that retroperitoneal adhesions were significantly reduced with the combination of the gel treatment and post lavage and the treatment with all three steps. Similarly, FIG. 2 shows that the liver adhesions were significantly reduced relative to the control in all testing except the intermediate application of NOCC gel alone.

These results as a whole show that the NOCC solution, when used as a post-surgical lavage, provides not just the advantages of minimizing on site adhesions but also minimizing off site adhesions resulting from the anastomosis. The NOCC gel alone does not appear to have the ability to do this. It is also significant to note that in all of the NOCC treated animals, the aortic anastomosis was in excellent shape. No evidence of degradation of the suture site was seen and no aneurysms or pseudoaneurysms were seen at or near the suture site. Accordingly, it is clear that the use of the NOCC solution, either alone or in combination with the pre-surgical lavage and the NOCC gel coating, provide significant benefits in minimizing problems associated with surgical adhesions.

EXAMPLE 3

This example illustrates the effect of utilizing NOCC in an intestinal anastomosis model, and the associated rate of healing. Peritonitis from leakage of normal intestinal flora into the peritoneal cavity following intestinal surgery is a significant problem in intestinal surgery. The faster the wound heals, the less the chance of peritonitis; therefore, it is beneficial to test whether the use of NOCC would impede the healing process. Although no delayed healing problem had been shown with the aortic anastomosis model, confirmation with the intestinal model showed similar beneficial effects.

Male Sprague-Dawley rats weighing approximately 250–300 g were anesthetized with sodium pentobarbital (20 mg/ml). A midline incision was made in the abdominal cavity and the abdomen was exposed with a stainless steel retractor, similar to the procedure described in Example 2. Again, the animals were eviscerated to the left and the viscera were covered with saline-soaked gauze. However, in this case the descending colon was left remaining in the cavity and a site approximately half way down the colon was selected for the surgical procedure. The colon was cleared of any remaining material by milking down before transection. The colon was completely transected and subsequently anastomosed with 6.0 sutures. The viscera were replaced in the abdominal cavity and the muscle wall and skin were sutured separately with running 3.0 sutures. All the test animals received 3 ml of a 2% NOCC solution immediately after opening the animal and immediately before closure. One ml of a covalently cross-linked NOCC gel was added after the anastomosis was complete, but before the post-surgical lavage. The control group received the same surgical technique but without the NOCC.

The animals were allowed to feed ad libitum immediately after surgery and six animals from each group were sacrificed on each of days 4, 7 and 14 post surgery. The colons were removed en bloc, adherent tissue was carefully removed from the colon, and a 5 cm section which included the anastomosis was obtained. One end of the colon was sewn closed with suture material and the other end was intubated with a small catheter. The catheter was fixed to the colon with sutures. The catheter was then attached to an infuser linked to a manometer. The specimen was placed under water and air was infused until bubbles appeared. The pressure required to cause the breakthrough bubbling was measured on the manometer. FIG. 3 shows the results of this test, in a plot of pressure in mm Hg versus days after surgery. As can be seen, there was no significant difference between the control and the NOCC treated animals in pressure readings on the healing anastomosis. These results confirm that the NOCC treatment does not interfere with normal healing of the surgical wound. Accordingly, although the NOCC appears to provide beneficial effects in treating adhesions, it does not impede the healing process at all.

The foregoing examples are merely exemplary and those skilled in the art will be able to determine other modifications to the described procedures which fall within the scope of the invention. Accordingly, the invention is defined by the following claims and equivalents thereof.

I claim:

1. A method of reducing post-surgical adhesions in a surgical patient comprising the sequential steps of (1) coating of a surgical site with an effective amount of a covalently crosslinked N,O-carboxymethylchitosan gel post-suturing, and (2) post-surgical lavage of said surgical site with a solution containing an effective amount of N,O-carboxymethylchitosan in a pharmaceutically acceptable carrier.

2. The method of claim 1 wherein said effective amount of N,O-carboxymethylchitosan in said post-surgical lavage solution is about 100–300 mg/kg of said surgical patient's body weight.

3. The method of claim 1 wherein said post-surgical lavage solution comprises 0.5–4% by weight N,O-carboxymethylchitosan.

4. The method of claim 3 wherein said post-surgical lavage solution comprises 1–3% by weight N,O-carboxymethylchitosan.

5. The method of claim 1 wherein said pharmaceutically acceptable carrier for said post-surgical lavage solution is selected from the group consisting of water, saline, phosphate buffered saline, and mixtures thereof.

6. The method of claim 1 wherein said covalently crosslinked N,O-carboxymethylchitosan gel comprises 0.1-3% N,O-carboxymethylchitosan by weight.

7. The method of claim 6 wherein said covalently crosslinked N,O-carboxymethylchitosan gel comprises 0.5-1.5% N,O-carboxymethylchitosan by weight.

8. The method of claim 1 further comprising the step of pre-surgical lavage with a solution containing an effective amount of N,O-carboxymethylchitosan in a pharmaceutically acceptable carrier.

9. The method of claim 8 wherein said effective amount of N,O-carboxymethylchitosan in said pre-surgical lavage is 100-300 mg/kg of said surgical patient's body weight.

10. The method of claim 8 wherein said pre-surgical lavage solution comprises 0.5-4% N,O-carboxymethylchitosan by weight.

11. The method of claim 10 wherein said pre-surgical lavage solution comprises 1-3% N,O-carboxymethylchitosan by weight.

12. The method of claim 8 wherein said pharmaceutically acceptable carrier for said pre-surgical lavage is selected from the group consisting of water, saline, phosphate buffered saline, and mixtures thereof.

13. A kit for post-surgical lavage of surgical incisions so as to reduce adhesions comprising a sterile 0.5-4% by weight solution of N,O-carboxymethylchitosan in a pharmaceutically acceptable carrier and a sterile gel for treating said surgical incisions prior to using the post-surgical lavage solution, said sterile gel comprising 0.1-3% by weight of covalently crosslinked, N,O-carboxymethylchitosan.

14. The kit of claim 13 wherein said pharmaceutically acceptable carrier is selected from the group consisting of water, saline, phosphate buffered saline, and mixtures thereof.

15. The kit of claim 13 further containing a sterile surgical gel for treating said surgical incisions prior to using the post-surgical lavage solution, said surgical gel comprising 0.1-10% by weight of a non-covalently complexed N,O-carboxymethylchitosan.

* * * * *